US006593500B2

(12) United States Patent
Priou et al.

(10) Patent No.: US 6,593,500 B2
(45) Date of Patent: Jul. 15, 2003

(54) PROCESS FOR ALKOXYLATION WITH A BORON-CONTAINING CATALYST

(75) Inventors: Christian B. Priou, West Windsor, NJ (US); Patricia Beurdeley, Paris (FR)

(73) Assignee: Rhodia, Inc., Cranbury, NJ (US)

(*) Notice: Subject to any disclaimer, the term of this patent is extended or adjusted under 35 U.S.C. 154(b) by 0 days.

(21) Appl. No.: 09/766,533

(22) Filed: Jan. 19, 2001

(65) Prior Publication Data

US 2002/0128521 A1 Sep. 12, 2002

(51) Int. Cl.[7] ................ C07C 41/03

(52) U.S. Cl. ................ 568/618; 568/678

(58) Field of Search ................ 568/618, 678

(56) References Cited

U.S. PATENT DOCUMENTS

| | | | |
|---|---|---|---|
| 3,471,411 A | 10/1969 | Bowman et al. | 252/431 |
| 3,969,417 A | 7/1976 | Umbach et al. | 260/615 B |
| 4,112,231 A | 9/1978 | Weibull et al. | 544/174 |
| 4,210,764 A | 7/1980 | Yang et al. | 568/618 |
| 4,223,163 A | 9/1980 | Guilloty | 568/618 |
| 4,223,164 A | 9/1980 | Nield et al. | 568/618 |
| 4,239,917 A | 12/1980 | Yang | 568/618 |
| 4,278,820 A | 7/1981 | Kametaka | 568/678 |
| 4,302,613 A | 11/1981 | Yang et al. | 568/618 |
| 4,306,093 A | 12/1981 | Yang et al. | 568/618 |
| 4,360,698 A | 11/1982 | Sedon | 568/618 |
| 4,396,779 A | 8/1983 | Edwards | 568/618 |
| 4,409,403 A | 10/1983 | Vaughan | 568/678 |
| 4,453,022 A | 6/1984 | McCain et al. | 568/618 |
| 4,453,023 A | 6/1984 | McCain et al. | 568/618 |
| 4,456,697 A | 6/1984 | Yang | 502/171 |
| 4,456,773 A | 6/1984 | Fock | 568/608 |
| 4,465,877 A | 8/1984 | Edwards | 568/618 |
| 4,483,941 A | 11/1984 | Yang | 502/171 |
| 4,543,430 A | 9/1985 | Falgoux et al. | 568/678 |
| 4,721,817 A | 1/1988 | Edwards | 518/618 |
| 4,727,199 A | 2/1988 | King | 568/620 |
| 4,754,075 A | 6/1988 | Knopf et al. | 568/618 |
| 4,762,952 A | 8/1988 | Green | 568/678 |
| 4,764,567 A | 8/1988 | Ott | 525/403 |
| 4,775,653 A | 10/1988 | Leach et al. | 502/170 |
| 4,832,321 A | 5/1989 | Aardema | 554/149 |
| 4,885,009 A | 12/1989 | Schneider | 55/96 |
| 5,220,046 A | 6/1993 | Leach et al. | 267/287 |

FOREIGN PATENT DOCUMENTS

| | | | | |
|---|---|---|---|---|
| EP | 1125961 A1 | * | 8/2001 | |
| JP | WO 00/02952 | | 1/2000 | C08G/65/26 |
| WO | WO 2000002952 | * | 1/2000 | |

* cited by examiner

*Primary Examiner*—Rosalynd Keys
(74) *Attorney, Agent, or Firm*—Ohlandt, Greeley, Ruggiero & Perle, L.L.P.

(57) ABSTRACT

Disclosed is a process for making alkoxylates of organic compounds. The process requires a) providing an active hydrogen organic compound having 1 to 22 carbon atoms, and b) alkoxylating the organic compound with an alkylene oxide in the presence of a catalytically effective amount of a catalyst compound corresponding to either formula (I) or formula (II):

$$B(\phi)_3 \quad (I)$$

$$H^+B(\phi)_4^- \quad (II)$$

wherein B is a boron atom and H is a hydrogen atom; $\phi$ is a phenyl moiety having substituents selected from the group consisting of 1 to 5 fluorine atoms, 1 to 5 $CF_3$ moieties, 1 to 5 $OCF_3$ or $SCF_3$ moieties or OR; wherein C is a carbon atom, O is an oxygen atom, S is a sulfur atom and F is a fluorine atom; wherein R is a hydrogen atom or an alkyl or aryl group having from 1 to 22 carbon atoms. The process affords a product of very narrow molecular weight distribution with a low degree of both residual active hydrogen organic starting material and undesirable by-products.

13 Claims, No Drawings

PROCESS FOR ALKOXYLATION WITH A BORON-CONTAINING CATALYST

BACKGROUND OF THE INVENTION

1. Field of the Invention

The invention relates to a process for making alkoxylated organic compounds of narrow molecular weight distribution. More particularly, the invention relates to a process for alkoxylation with alkylene oxides in the presence of a boron-containing catalyst.

2. Background of the Invention

Nonionic surfactants are industrially manufactured by reaction of a organic compound with ethylene oxide using a base as catalyst e.g. sodium or potassium hydroxide. Nonionic surfactants are commonly manufactured from the ethoxylation of fatty alcohols.

When a relatively low degree of ethoxylation, i.e. one to four moles, is desired, an undesirably broad molecular weight product distribution is obtained. The broad distribution is due to the similar basicity of the alcohol and ethoxylate. Additive ethoxylation proceeds at the expense of ethoxylation of alcohol. Consequently, low mole ethoxylate products typically have relatively large amounts of unreacted alcohol. Residual alcohol in the product presents odor problems and reduces the smoke point. A low smoke point is especially problematic during the spray-drying of powdered detergents containing ethoxylated nonionic surfactants, when a low smoke point may result in undesirable volatilization of the surfactants.

In addition to higher smoke points and lower odor, ethoxylates of narrow molecular weight distribution have performance advantages over ethoxylates of broad molecular weight distribution. They include the following: (i) lower viscosity and pour point for easier handling; (ii) higher cloud point; (iii) higher initial foaming and less foam stability; (iv) better wetting properties; (v) increased interfacial surface tension reduction compared to paraffin; and (vi) higher surface tension than conventional ethoxylates.

Various processes have been proposed in the base catalysis art to reduce the molecular weight distribution of alkoxylates. Such art is seen, for example, in U.S. Pat. Nos. 3,471,411; 3,969,417; 4,112,231; 4,210,764; 4,223,163; 4,223,164; 4,239,917; 4,278,820; 4,302,613; 4,306,093; 4,360,698; 4,396,779; 4,453,022; 4,465,877; 4,453,023; 4,456,773; 4,456,697; 4,721,817; 4,727,199; 4,754,075; 4,764,567; 4,775,653; 4,885,009; 4,832,321 and 5,220,046, which are incorporated herein by reference. However, the art has to date failed to propose a base catalysis process for making alkoxylates of sufficiently narrow molecular weight distribution.

One means for making alkoxylates of narrower molecular weight distribution is to employ acid catalysis to effect polymerization. Acid catalysis has been generally disfavored, however, in the art because of the formation of relatively high levels of undesirable by-products. For instance, polyoxyethylene is formed by competing dehydration reactions and dioxane and 2-methyldioxolane are formed by competing cyclization reactions.

Processes for making alkoxylates of narrow molecular weight range with catalysts of perfluorosulfonic acid derivatives have been proposed. U.S. Pat. No. 4,483,941 discloses the use of catalyst mixtures of boron fluorides and metal alkoxides. U.S. Pat. No. 4,762,952 discloses the use of boron salts of perfluorosulfonic acid polymer. U.S. Pat. No. 4,409,403 relates to the use of a polyfluorosulfonic acid catalysts. U.S. Pat. No. 4,543,430 relates to the use of trifluoromethane sulfonic acid with Group II metals, specifically aluminum, cobalt, nickel, zirconium and tin.

It would be desirable to have a new and effective process for making alkoxylates of still narrower molecular weight distribution. Further, it would be desirable to have a process which afforded a still lower degree of residual active hydrogen organic starting material. Still further, it would be desirable to have a process which afforded a lower degree of undesirable by-products.

SUMMARY OF THE INVENTION

It is an object of the present invention to produce alkoxylated organic compounds of narrow molecular weight distribution.

It is a further object of the present invention to produce alkoxylated organic compounds and leave relatively low proportions of residual starting materials.

It is still a further object of the present invention to produce alkoxylated organic compounds with relatively low proportions of undesirable by-products.

It is still a further object of the invention to have a process for making alkoxylates of active hydrogen organic compounds requiring (a) providing an active hydrogen organic compound having an alkyl group of about 8 to about 20 carbon atoms and (b) alkoxylating the organic compound with an alkylene oxide in the presence of a catalytically effective amount of a catalyst compound corresponding to formula (I) and formula (II):

$$B(\phi)_3 \quad (I)$$

$$H^+B(\phi)_4^- \quad (II)$$

wherein B is a boron atom and H is a hydrogen atom; $\phi$ is a phenyl moiety having substituents selected from the group consisting of 1 to 5 fluorine atoms, 1 to 5 $CF_3$ moieties, 1 to 5 $OCF_3$ or $SCF_3$ moieties or OR; wherein C is a carbon atom, O is an oxygen atom, S is a sulfur atom and F is a fluorine atom; wherein R is a hydrogen atom or an alkyl or aryl group having from 1 to 22 carbon atoms. The process affords a product of very narrow molecular weight distribution with a low degree of both residual active hydrogen organic starting material and undesirable by-products.

DETAILED DESCRIPTION OF THE INVENTION

In the process of the present invention, it was found surprising that alkoxylates of narrow molecular weight distribution could be prepared using certain boron catalysts. It was also surprising that such alkoxylates could be prepared leaving a relatively low degree of residual active hydrogen organic starting material and undesirable by-products.

The present process employs a catalyst compound corresponding to either formula (I) or formula (II):

$$B(\phi)_3 \quad (I)$$

$$H^+B(\phi)_4^- \quad (II)$$

wherein B is a boron atom and H is a hydrogen atom; $\phi$ is a phenyl moiety having substituents selected from the group consisting of 1 to 5 fluorine atoms, 1 to 5 $CF_3$ moieties, 1 to 5 $OCF_3$ or $SCF_3$ moieties or OR; wherein C is a carbon atom, O is an oxygen atom, S is a sulfur atom and F is a fluorine atom; wherein R is a hydrogen atom or an alkyl or aryl group having from 1 to 22 carbon atoms.

Representative catalyst compounds corresponding to formula (I) include tris(pentafluorophenyl)borane, tris(2,4,6-trifluorophenyl)borane, tris(4-fluorophenyl)borane, tris(3,5 di(trifluoromethyl)phenyl)borane and tris(3,5-difluorophenyl)borane. The preferred catalyst compound is tris(pentafluorophenyl)borane.

Representative catalyst compounds corresponding to formula (II) include $HB(C_6F_5)_3OH$ and $HB(C_6F_5)_3OCH_3$. Others include tetrakis(pentafluorophenyl) borate ($HB(C_6F_5)_4$) and tetrakis(2,4-di(trifluoromethyl)phenyl) borate ($HB(C_6H_3(CF_3)_2)_4$.

A most preferred catalyst is tris(pentafluorophenyl) borane. Tris(pentafluorophenyl)borane has the following structure:

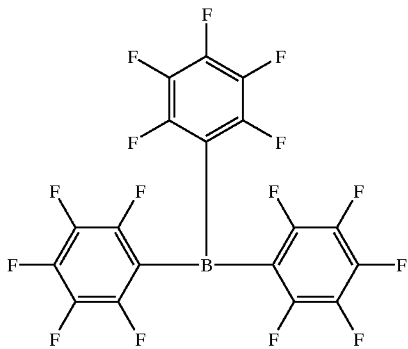

The catalyst is employed in the process at about $1.0\times10^{-6}$M to about $1.0\times10^{-1}$M based on the organic compound.

The active hydrogen organic compound employed in the present process has from 1 to 22 carbon atoms. Useful active hydrogen organic compounds include alcohols, amines, mercaptans and amides. Preferred compounds are hydrophobic and have from 1 to 22 carbon atoms. Preferred compounds are also hydroxylated. Preferred hydroxylated compounds include fatty alcohols. Fatty alcohols can be obtained from natural sources such as fats and oils or may be derived synthetically from petroleum. Natural alcohols are prepared from natural fatty acids derived from coconut oil, palm kernel oil, palm oil, tallow, soya, sperm oils and the like. Useful fatty alcohols include octanol, nonanol, decanol, dodecanol, palmityl alcohol, octadecanol, eicosanol, behenyl alcohol, and stearyl alcohol and mixtures or blends of the foregoing. A preferred fatty alcohol is dodecanol. Unsaturated alcohols such as oleoyl, linoleic and linolenic alcohols are also useful. Synthetic alcohols may be prepared using the oxo (hydroformylation of carbon monoxide and hydrogen) or the Ziegler (ethylene and triethylaluminum) processes. Typical alcohols are oxodecyl, oxotridecyl, oxotetradecyl alcohol. Useful alcohols include Neodol 23, 25 and 91 (Shell Corp.). Aromatic alcohols are also useful. Typical aromatic alcohols are nonylphenol, octylphenol diisobutylphenol, dodecylphenol and dinonylphenol. Useful low molecular weight alcohols, include methanol, ethanol, propanol, butanol and other $C_1$ to $C_7$ alcohols.

Alkoxylation is carried out by contacting the active hydrogen organic compound with an alkylene oxide under catalytically effective conditions. The catalysis is carried out in the presence of tris(pentafluorophenyl)borane, which is a Lewis acid. The alkoxylation reaction can be carried out in temperature conditions from about 20° C. to 200° C.

Alkoxylation is carried out by contacting the active hydrogen organic compound with 1 to 100 moles of alkylene oxide per mole of organic compound. Alkoxylation can also be carried out by contacting the active hydrogen organic compound with 2 to 4 moles of alkylene oxide per mole of organic compound.

Alkoxylation include the reactions of ethoxylation, propoxylation, and butoxylation. Alkoxylation reactions involving adducts of higher numbers of carbons are possible and within the scope of the invention. Useful alkylene oxides include but are not limited to ethylene oxide, propylene oxide, butylene oxide and cyclohexene oxide. An important reaction industrially is ethoxylation, which typically involves the addition of ethylene oxide to a organic compound. More specifically, an important reaction is the polyethoxylation of dodecanol.

The present process affords the production of product having relatively narrow molecular weight distribution. Although not bound by any particular range or level of distribution, degrees of narrowing up to about 95% are possible. A preferred range is about 80 to about 95%. Degree of narrowing can be determined according to the formula and method set forth below.

The present process affords advantages over conventional base catalysis of the prior art. The present process yields alkoxylated product of considerably narrower molecular weight distribution than that produced by conventional base catalysis using potassium or sodium hydroxide. Further, the present process leaves a lower residual content of active hydrogen organic starting material, i.e. fatty alcohols, than conventional base catalysis. Further, the present process can be effected at a lower operating temperatures than with conventional base catalysis. Still further, the present process can be effected with about a tenth of the amount of catalyst normally employed in conventional base catalysis.

The present process affords advantages over prior art acid catalysis carried out in the presence of perfluorosulfonic acid derivatives. The present process produces alkoxylates of narrower molecular weight distribution with lower levels of residual starting materials and by-products.

The catalyst can be used as is or can be supported on a mineral charge such as silica, alumno, titanium dioxide and the like. The catalyst can be left in the final product or be recycled after proper treatment.

The following are non-limiting examples of the present invention. All percentages are by weight unless indicated otherwise.

EXAMPLES

Ethoxylates were prepared according to the process of the present invention via catalysis with tris(pentafluorophenyl) borane. The relative degrees of narrowing, residual starting material content, and by-product content were measured. The results were compared to ethoxylates prepared via conventional base catalysis.

The degree of narrowing was defined according to the following formula:

$$\text{Degree of Narrowing}: DN = \sum_{n=n\max-2}^{n=n\max-2} Yi$$

wherein n max=the molar number of added ethylene oxide (or alkylene oxide) in an adduct accounting for a maximum proportion by weight in a total adduct.

Yi=proportion by weight of an adduct having "i" moles of added ethylene oxide to a total weight of the adduct.

For degree of narrowing determination, the gas chromatographic (GC) area % was used. The degree of narrowing is expressed as a percentage (%). The higher the percentage, the narrower the molecular weight distribution. The formula and method are set forth in *Narrow Alcohol Ethoxylates*, Annual Surfactants Reviews, vol. 2, Ed. D. R. Karsa (1999).

Comparative Example

In this comparative example, ethylene oxide was reacted with dodecanol on a 3:1 mole basis in the presence of a potassium hydroxide catalyst. Dodecanol [Aldrich, 98%+ reagent) at 199.7 grams (gm) (1.07 moles)] and 3.56 gm of potassium hydroxide (45%, 1.6 gm as 100%) were charged to a two liter autoclave. The autoclave was heated with nitrogen sparge to 120° C. The autoclave was vacuum stripped for one hour with a slight nitrogen sparge. The vacuum was secured, then the autoclave was pressurized to 20 psig with nitrogen and heated to 150° C. Ethylene oxide (141.5 gm (3.21 moles)) was added over a one hour period at 150° C. and 50 pounds per square inch gauge (psig) and held for an additional hour. The autoclave was then cooled to 120° C. and vacuum stripped for ten minutes. The autoclave was then cooled and 321 gm of product discharged. The product had a degree of narrowing of 62.4% and contained 12.6% residual dodecanol and 1.7% by-product polyethylene glycol.

Example 1

In this example, ethylene oxide was reacted with dodecanol on a 3:1 mole basis in the presence of a trispentafluorophenylboron catalyst. Dodecanol at 198.9 gm (1.08 moles) and trispentafluorophenylboron at $2.89\times10^{-3}$ moles were charged to a two liter autoclave. The autoclave was then heated to 120° C. with a nitrogen sparge. The autoclave was then vacuum stripped for one hour at 120° C. with a slight nitrogen sparge. The autoclave was then heated to 150° C. and pressurized to 20 psig with nitrogen blanket and 186.0 gm (4.22 moles) of ethylene oxide was added at 50 psig over a one hour period. The autoclave was then cooled to 120° C. and vacuum stripped for ten (10) minutes, cooled and 370 gm of product discharged.

The product exhibited a higher degree of narrowing (82.5% versus 62.4%) and lower residual dodecanol content (2.9% versus 12.6%) than the Comparative Example. The product also exhibited a low by-product content, 0.03% dioxane and 1.5% polyethylene glycol (PEG).

Example 2

Dodecanol (Aldrich) (197.6 gm (1.08 moles)) and Trispentafluorophenylboron at 0.264 mole percent were charged to a two liter autoclave. The autoclave was then heated to 120° C. and purged one hour under vacuum with a nitrogen sparge. The autoclave was then cooled to 45° C. and pressurized to 20 psig with nitrogen. Ethylene oxide (139 gm (3.22 moles)) was then added to the autoclave over a 2½ hour period. Residual ethylene oxide was purged from the autoclave over a two (2) hour period to yield 318 gm of product.

The product exhibited a higher degree of narrowing (81% versus 62.4%) and lower residual dodecanol content (5% versus 12.6%) than the Comparative Example. The product also exhibited a low by-product content, 0.13% dioxane and 1.1% polyethylene glycol (PEG). The product was colorless.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A process for making alkoxylates of organic compounds, comprising:

a) providing an active hydrogen organic compound having 1 to 22 carbon atoms and b) alkoxylating the active hydrogen organic compound with an alkylene oxide in the presence of a catalytically effective amount of a catalyst compound corresponding to formula (II):

$$H^+B(\phi)_4^- \quad \text{(II)}$$

wherein B is a boron atom and H is a hydrogen atom; $\phi$ is a phenyl moiety having substituents selected from the group consisting of 1 to 5 fluorine atoms, 1 to 5 $CF_3$ moieties, 1 to 5 $OCF_3$ or $SCF_3$ moieties or OR; wherein C is a carbon atom, O is an oxygen atom, S is a sulfur atom and F is a fluorine atom; wherein R is a hydrogen atom or an alkyl or aryl group having from 1 to 22 carbon atoms.

2. The process of claim 1, wherein the catalyst compound is $HB(C_6F_5)_4$.

3. The process of claim 1, wherein the catalyst compound is selected from the group consisting of tetrakis (pentafluorophenyl)borate ($HB(C_6F_5)_4$) and tetrakis (2,4-di (trifluoromethyl)phenyl)borate acid ($HB(C_6H_3(CF_3)_2)_4$.

4. The process of claim 1, wherein the organic compound is a fatty alcohol.

5. The process of claim 4, wherein the fatty alcohol is dodecanol.

6. The process of claim 1, wherein the catalyst is present at about $1.0\times10^{-6}$ M to about $1.0\times10^{-1}$ M based on the organic compound.

7. The process of claim 1, wherein the alkoxylation is carried out at from about 20° C. to 200° C.

8. The process of claim 1, wherein 1 to 100 moles of alkylene oxide per mole of organic compound are reacted during alkoxylation.

9. The process of claim 1, wherein 2 to 4 moles of alkylene oxide per mole of organic compound are reacted during alkoxylation.

10. The process of claim 1, wherein the alkylene oxide is ethylene oxide.

11. The process of claim 1, wherein the active hydrogen organic compound is a fatty alcohol having from 8 to 22 carbon atoms, the catalyst being present at about $1.0\times10^{-6}$ M to about $1.0\times10^{-}$M based on the fatty alcohol, the alkylene oxide being ethylene oxide, the alkoxylation being carried out at from about 20° C. to 170° C., 1 to 100 moles of ethylene oxide per mole of the active hydrogen organic compound are reacted during alkoxylation.

12. The process of claim 11, wherein the fatty alcohol is dodecanol.

13. The process of claim 12, wherein 2 to 4 moles of alkylene oxide per mole of fatty alcohol are reacted during alkoxylation.

* * * * *